(12) United States Patent
Williams et al.

(10) Patent No.: US 9,687,334 B2
(45) Date of Patent: Jun. 27, 2017

(54) INTESTINAL SLEEVES AND ASSOCIATED DEPLOYMENT SYSTEMS AND METHODS

(75) Inventors: Michael S. Williams, Santa Rosa, CA (US); Daniel W. Fifer, Windsor, CA (US); Geoffrey A. Orth, Sebastopol, CA (US); Jeffrey A. Smith, Petaluma, CA (US); Richard A. Glenn, Chapel Hill, NC (US); William L. Athas, Chapel Hill, NC (US); Richard S. Stack, Chapel Hill, NC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1150 days.

(21) Appl. No.: 13/353,258

(22) Filed: Jan. 18, 2012

(65) Prior Publication Data

US 2012/0116286 A1    May 10, 2012

Related U.S. Application Data

(62) Division of application No. 11/897,701, filed on Aug. 31, 2007, now Pat. No. 8,109,895.

(Continued)

(51) Int. Cl.
*A61M 5/00* (2006.01)
*A61F 2/04* (2013.01)
(Continued)

(52) U.S. Cl.
CPC ........ *A61F 2/04* (2013.01); *A61F 2/07* (2013.01); *A61F 2/95* (2013.01); *A61F 5/0076* (2013.01);
(Continued)

(58) Field of Classification Search
CPC .................. A61F 5/0076; A61F 5/0036; A61F 2002/045; A61F 5/0089; A61F 5/0013; A61F 2/95; A61F 2/04
(Continued)

(56) References Cited

U.S. PATENT DOCUMENTS

| 1,408,865 A | 3/1922 | Cowell |
| 3,663,965 A | 5/1972 | Lee et al. |

(Continued)

FOREIGN PATENT DOCUMENTS

| CH | 680263 A5 | 7/1992 |
| EP | 0 775 471 A1 | 5/1997 |

(Continued)

OTHER PUBLICATIONS

International Search Report from PCT Patent Application No. PCT/US2002/027177 mailed Feb. 14, 2003.
(Continued)

*Primary Examiner* — Tatyana Zalukaeva
*Assistant Examiner* — Ariana Zimbouski
(74) *Attorney, Agent, or Firm* — Bookoff McAndrews, PLLC

(57) ABSTRACT

An intestinal implant includes a proximal anchor self-expandable from a radially compressed position to a radially expandable position for engagement with a wall of the intestinal lumen and a flexible sleeve coupled to the anchor. The sleeve is implanted with the anchor downstream from the pylorus and the sleeve extending further downstream through the intestinal lumen.

15 Claims, 12 Drawing Sheets

Related U.S. Application Data

(60) Provisional application No. 60/824,435, filed on Sep. 2, 2006.

(51) Int. Cl.
 *A61F 2/07* (2013.01)
 *A61F 2/95* (2013.01)
 *A61F 5/00* (2006.01)

(52) U.S. Cl.
 CPC ... *A61F 2002/044* (2013.01); *A61F 2002/045* (2013.01)

(58) Field of Classification Search
 USPC ........................................................ 623/1.11
 See application file for complete search history.

(56) References Cited

U.S. PATENT DOCUMENTS

| | | | |
|---|---|---|---|
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shlain |
| 5,355,897 A | 10/1994 | Pietrafitta et al. |
| 5,401,241 A | 3/1995 | Delany |
| 5,403,326 A | 4/1995 | Harrison et al. |
| 5,405,377 A | 4/1995 | Cragg |
| 5,431,673 A | 7/1995 | Summers et al. |
| 5,486,187 A | 1/1996 | Schenck |
| 5,514,176 A | 5/1996 | Bosley, Jr. |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,792,119 A | 8/1998 | Marx |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | LoCicero, III |
| 5,897,562 A | 4/1999 | Bolanos et al. |
| 5,910,144 A | 6/1999 | Hayashi |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egres, Jr. |
| 6,051,015 A | 4/2000 | Maahs |
| 6,086,600 A | 7/2000 | Kortenbach |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman et al. |
| 6,416,522 B1 | 7/2002 | Strecker |
| 6,425,916 B1 | 7/2002 | Garrison et al. |
| 6,454,785 B2 | 9/2002 | De Hoyos Garza |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer et al. |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor et al. |
| 6,572,627 B2 | 6/2003 | Gabbay |
| 6,572,629 B2 | 6/2003 | Kalloo |
| 6,575,896 B2 | 6/2003 | Silverman |
| 6,592,596 B1 | 7/2003 | Geitz |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |

(56) References Cited

U.S. PATENT DOCUMENTS

| | | |
|---|---|---|
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapacki et al. |
| 7,033,373 B2 | 4/2006 | de la Torre et al. |
| 7,033,384 B2 | 4/2006 | Gannoe et al. |
| 7,056,305 B2 | 6/2006 | Garza |
| 7,066,945 B2 | 6/2006 | Hashiba et al. |
| 7,083,629 B2 | 8/2006 | Weller et al. |
| 7,090,699 B2 | 8/2006 | Geitz |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,122,058 B2 | 10/2006 | Levine et al. |
| 7,147,140 B2 | 12/2006 | Wukusick et al. |
| 7,160,312 B2 | 1/2007 | Saadat et al. |
| 7,172,613 B2 | 2/2007 | Wazne |
| 7,175,660 B2 | 2/2007 | Cartledge et al. |
| 7,211,114 B2 | 5/2007 | Bessler et al. |
| 7,214,233 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,335,210 B2 | 2/2008 | Smit |
| 7,354,454 B2 | 4/2008 | Stack et al. |
| 7,431,725 B2 | 10/2008 | Stack et al. |
| 7,608,114 B2 | 10/2009 | Levine et al. |
| 7,695,446 B2 | 4/2010 | Levine et al. |
| 7,819,836 B2 | 10/2010 | Levine et al. |
| 7,881,797 B2 | 2/2011 | Griffin et al. |
| 7,892,214 B2 | 2/2011 | Kagan et al. |
| 7,931,693 B2 * | 4/2011 | Binmoeller ............ A61F 5/003 606/191 |
| 8,020,741 B2 | 9/2011 | Cole et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 | 6/2002 | Schurr et al. |
| 2002/0099439 A1 | 7/2002 | Schwartz et al. |
| 2002/0183767 A1 | 12/2002 | Adams et al. |
| 2002/0183768 A1 | 12/2002 | Deem et al. |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120289 A1 | 6/2003 | McGuckin, Jr. et al. |
| 2003/0158569 A1 | 8/2003 | Wazne |
| 2003/0191476 A1 * | 10/2003 | Smit ................ A61B 17/00491 606/108 |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 | 3/2004 | DeVries et al. |
| 2004/0082963 A1 | 4/2004 | Gannoe et al. |
| 2004/0088023 A1 | 5/2004 | Imran et al. |
| 2004/0092892 A1 * | 5/2004 | Kagan ...................... A61F 2/04 604/264 |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 * | 6/2004 | Levine et al. ............ 623/23.64 |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 | 3/2005 | Dann et al. |
| 2005/0055039 A1 * | 3/2005 | Burnett ............ A61B 5/14539 606/151 |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0216040 A1 | 9/2005 | Gertner et al. |
| 2005/0216042 A1 | 9/2005 | Gertner |
| 2005/0240279 A1 | 10/2005 | Kagan et al. |
| 2005/0247320 A1 | 11/2005 | Stack et al. |
| 2005/0250980 A1 | 11/2005 | Swanstrom et al. |
| 2005/0251158 A1 | 11/2005 | Saadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267405 A1 | 12/2005 | Shah |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 * | 12/2005 | Levy et al. .................... 604/192 |
| 2006/0009858 A1 * | 1/2006 | Levine ...................... A61F 2/04 623/23.65 |
| 2006/0015006 A1 | 1/2006 | Laurence et al. |
| 2006/0020278 A1 | 1/2006 | Burnett et al. |
| 2006/0058829 A1 | 3/2006 | Sampson et al. |
| 2006/0064120 A1 | 3/2006 | Levine et al. |
| 2006/0069400 A1 | 3/2006 | Burnett et al. |

(56) References Cited

U.S. PATENT DOCUMENTS

| | | |
|---|---|---|
| 2006/0129094 A1 | 6/2006 | Shah |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0155312 A1 | 7/2006 | Levine et al. |
| 2006/0161139 A1 | 7/2006 | Levine et al. |
| 2006/0161187 A1 | 7/2006 | Levine et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0276432 A1 | 11/2007 | Stack et al. |
| 2008/0065122 A1 | 3/2008 | Stack et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0294179 A1 | 11/2008 | Balbierz et al. |
| 2009/0024143 A1 | 1/2009 | Crews et al. |
| 2009/0030284 A1 | 1/2009 | Cole et al. |
| 2009/0125040 A1 | 5/2009 | Hambly et al. |
| 2009/0177215 A1 | 7/2009 | Stack et al. |

FOREIGN PATENT DOCUMENTS

| | | |
|---|---|---|
| EP | 1492478 | 1/2005 |
| EP | 1 602 336 A2 | 12/2005 |
| FR | 2768324 A1 | 3/1999 |
| JP | 09-168597 | 6/1997 |
| WO | WO 91/01117 A1 | 2/1991 |
| WO | WO 97/47231 A2 | 12/1997 |
| WO | WO 00/12027 A1 | 3/2000 |
| WO | WO 00/32137 A1 | 6/2000 |
| WO | WO 00/78227 A1 | 12/2000 |
| WO | WO 01/41671 | 6/2001 |
| WO | WO 01/45485 A2 | 6/2001 |
| WO | WO 01/49359 A1 | 7/2001 |
| WO | WO 01/66018 A1 | 9/2001 |
| WO | WO 01/85034 A1 | 11/2001 |
| WO | WO 01/89393 A1 | 11/2001 |
| WO | WO 02/060328 A1 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 A2 | 11/2003 |
| WO | WO 03/094785 | 11/2003 |
| WO | WO 03/099137 A2 | 12/2003 |
| WO | WO 2004/019765 | 3/2004 |
| WO | WO 2004/019787 | 3/2004 |
| WO | WO 2004/032760 A2 | 4/2004 |
| WO | WO 2004/037064 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 A1 | 12/2004 |
| WO | WO 2005/037152 A1 | 4/2005 |
| WO | WO 2005/079673 A2 | 9/2005 |
| WO | WO 2005/096991 A1 | 10/2005 |
| WO | WO 2005/105003 | 11/2005 |
| WO | WO 2006/016894 A1 | 2/2006 |
| WO | WO 2006/055365 A2 | 5/2006 |
| WO | WO 2006/127593 | 11/2006 |
| WO | WO 2007/041598 A1 | 4/2007 |

OTHER PUBLICATIONS

International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search report and Written Opinion for PCT application PCT/US2008/008726, Oct. 16, 2008, 13 pages (2008).
International Search report and Written Opinion for PCT application PCT/US2007/019833, Dec. 9, 2007, 11 pages (2007).
International Search report for PCT application PCT/US2008/063440, search report dated Aug. 1, 2008, 11 pages (2007).
International Search report and Written Opinion for PCT application PCT/US2007/019940, Mar. 20, 2008, 12 pages (2008).
Felsher, et al., "Mucosal apposition in endoscopic suturing", Gastrointestinal Endoscopy, vol. 58, No. 6, pp. 867-870, (2003).
Stecco, K. et al., "Trans-Oral Plication Formation and Gastric Implant Placement in a Canine Model", Stecco Group, San Jose and Barosnese, Inc., Redwood City, California (2004).
Stecco, K. et al., "Safety of A Gastric Restrictive Implant in a Canine Model", Stecco Group, San Jose and Barosnese, Inc., Redwood City, California (2004).

* cited by examiner

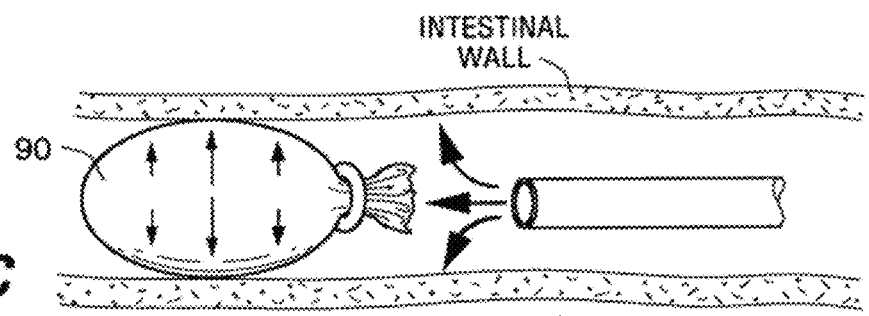
FIG. 22C
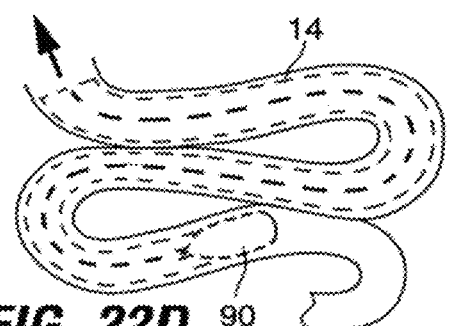
FIG. 22D
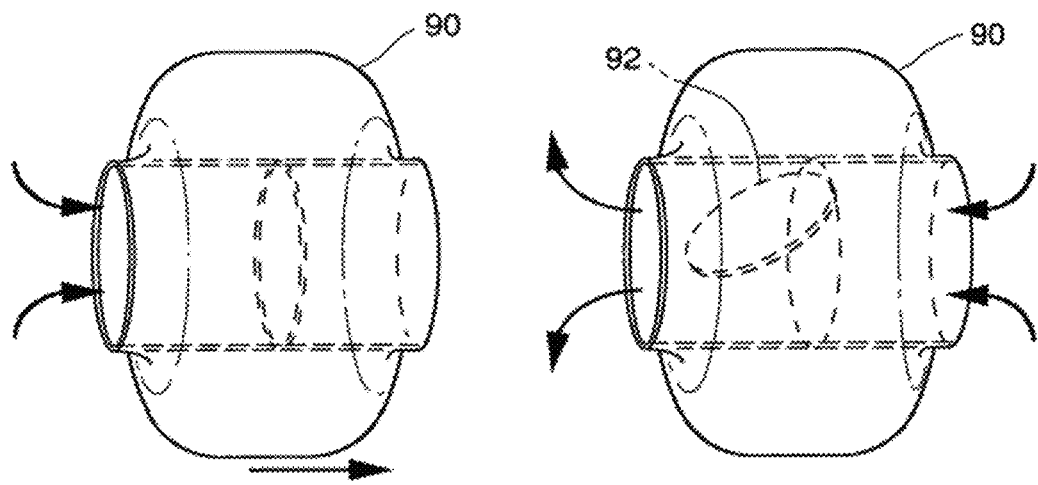
FIG. 23A
FIG. 23B
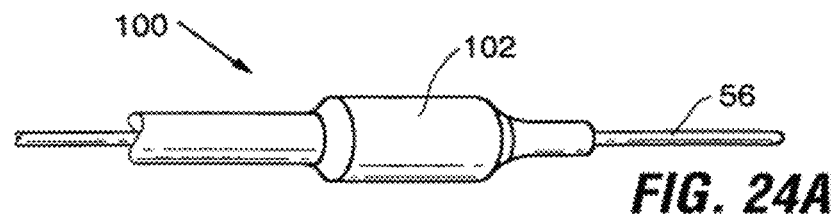
FIG. 24A

INTESTINAL SLEEVES AND ASSOCIATED DEPLOYMENT SYSTEMS AND METHODS

RELATED APPLICATIONS

This application is a divisional of U.S. application Ser. No. 11/897,701, filed Aug. 31, 2007, now allowed, which claims the benefit of U.S. Provisional Application No. 60/824,435, filed Sep. 2, 2006, each of which is herein incorporated by reference in its entirety.

FIELD OF THE INVENTION

The present invention relates to the field of implants for inducing weight loss in obese patients and/or treating Type II diabetes. More particularly, the invention relates to systems for implanting sleeves used to restrict intestinal absorption of ingested food and/or to regulate hormone release.

BACKGROUND OF THE INVENTION

An anatomical view of a human stomach S and associated features is shown in FIG. 27. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end.

Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

When food is placed in the mouth, carbohydrates in the food are partially broken down by enzymes in saliva. After the food is swallowed it is turned to a liquefied mass (chyme) by the acids and enzymes within the stomach. The chyme moves from the stomach into the intestine, where the chyme is further digested and where the bulk of the nutrients are absorbed through the intestinal membranes into the circulatory system. Within the small intestine, nutrients are broken down by enzymes and secretions from the pancreas, liver, gallbladder, as well as those secreted by cells of the intestine. The intestinal walls are lined with villi-small projections that extend into the intestinal lumen. The presence of the villi facilitates absorption by increasing the surface area of the small intestine. Undigested chyme passes into the large intestine (colon), from which it is ultimately excreted.

Prior patents and applications assigned to the assignee of the present application disclose the use of elongated intestinal sleeves or tubes for inducing weight loss. For example, U.S. Pat. No. 6,675,809 entitled "Satiation Device and Methods" describes, among other things, a tube that may be positioned beyond the pyloris, such as in or near the duodenum. Post-pyloric sleeves of this type can be useful for preventing or limiting absorption of nutrients by the small intestine, thus triggering weight loss in the patient.

Moreover, it has been reported that gastric bypass procedures in which a portion of the small intestine is bypassed can ameliorate Type 2 diabetes. F. Rubino et al, The Mechanism of Diabetes Control After Gastrointestinal Bypass Surgery Reveals a Role of the Proximal Small Intestine in the Pathophysiology of Type 2 Diabetes, Annals of Surgery, Vol. 243, Number 6, June 2006. Positioning a bypass sleeve of the type disclosed in the '809 patent in the small intestine of a patient can achieve the same therapeutic function in a much less invasive manner.

BRIEF DESCRIPTION OF THE DRAWINGS

FIGS. 20 and 21 show a modification to the system of FIG. 19, in which FIG. 20 shows the system collapsed within a tube for delivery into the stomach and through the pylorus, and FIG. 21 shows the system released from the tube.

FIGS. 22A-22D illustrate use of an alternative embodiment of a fluid deployable device for carrying a post-pyloric sleeve through the small intestine.

FIGS. 23A and 23B are perspective views showing a device similar to the FIG. 22A device modified to include a valve.

FIGS. 24A-24C illustrate a system for deploying a guide wire through an intestinal lumen.

DETAILED DESCRIPTION

This application describes intestinal sleeves, preferably anchored in the gastrointestinal track downstream of the pylorus, that are suitable for minimizing absorption of ingested materials including sugars, by the intestine, thus inducing weight loss and treating Type II diabetes.

Figure 1A:
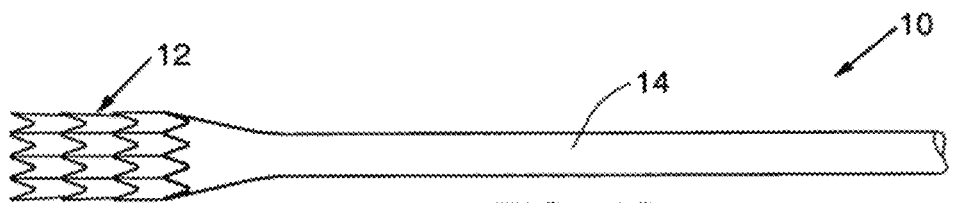
FIG. 1A is an elevation view of an example of a post-pyloric sleeve.
Figure 1B:
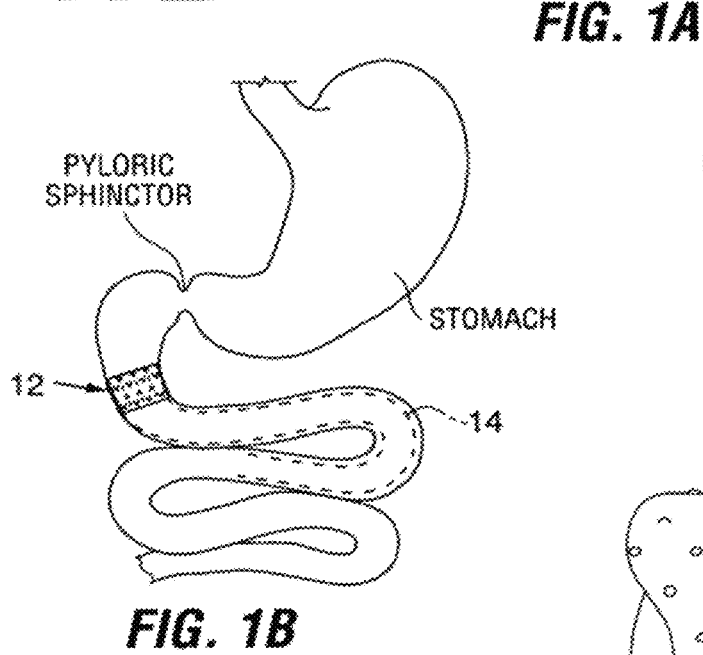
FIG. 1B schematically illustrates the post-pyloric sleeve of FIG. 1A within the small intestine.

FIG. 1A shows an example of a post-pyloric implant 10. Implant 10 includes an anchor 12 and an elongate flexible sleeve 14. The anchor 12 includes structural features that allow the anchor to be compressed to a small diameter for passage through the pylorus and into the small intestine, and then radially self-expanded into engagement with the wall of the intestinal lumen. Anchors constructed of mesh, bands or other structural frameworks using shape memory elements (e.g. nickel titanium alloy, nitinol or shape memory polymer) or stainless steel, Eligoy, or MP35N wires or structures may be used.

Sleeve 14 is preferably a flexible tube having a length chosen to limit absorption of nutrients by the small intestine. Exemplary devices may have lengths on the order of 10-200 cm, although longer or shorter devices might be suitable for certain patients. Materials suitable for use include ePTFE, polyurethane, microporous polyurethane, polyester, polyethylene and other comparable materials. The sleeve may be comprised of more than one material, for example the polymeric material may be reinforced with a metallic or polymeric braid or coil, or a braid or woven sleeve might include a polyurethane coating. In one embodiment, an ePTFE sleeve includes an elastomeric outer surface. A sleeve having this configuration can dwell in a partially collapsed state within the intestine, and then radially expand as food is driven through it by peristalsis. With this construction, the sleeve can resist twisting, kinking or collapse. It may also allow for passage of digestive enzymes along the exterior of the sleeve, and it can also facilitate deployment by natural means such as peristalsis if desired.

The materials or material properties of the sleeve may vary along the length of the sleeve. The inner and/or outer walls might be coated, treated or impregnated with any number of materials, coatings, or compositions, including hydrophilic coatings to enhance the lubricity of the sleeve, antimicrobial coatings, compositions that will regulate hormone production, etc. The sleeve may be non-porous, porous, or porous at certain locations.

Figure 1C:
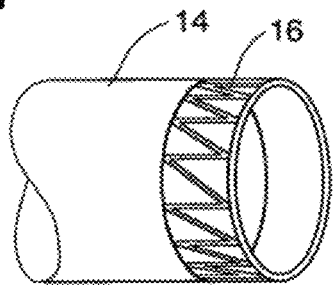
FIG. 1C illustrates an expanding feature that may be provided on the distal end of the sleeve of FIG. 1A.
Figure 1D:
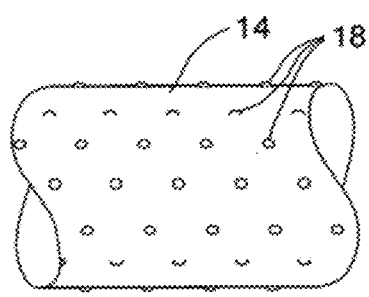
FIG. 1D illustrates external wall features that may be provided on the sleeve of FIG. 1A.

Openings may be positioned on the sleeve at select locations, such as at a location corresponding to the location of the common bile duct within the small intestine. As shown in FIG. 1C, the distal end of the sleeve 14 may include an embedded feature such as elastomeric scaffold 16 to facilitate opening of the distal end of the sleeve 14 to prevent obstruction. As illustrated in FIG. 1D, the exterior surface of the sleeve may include features 18 or a coating that allows the intestinal wall to lightly engage the sleeve, such as for preventing migration of the sleeve towards the stomach. These features might include nodules, barbs, spikes, dimples or other elements that provide texture to the sleeve.

Various methods for deploying an implant such as the implant 10 will next be described. For many of the disclosed methods, a deployment system is advanced through the pyloric sphincter and then used to deploy the sleeve with the anchor in a post-pyloric location and the sleeve extending distally of the anchor. These embodiments may be modified to position the anchor within the antrum or other parts of the stomach, with the sleeve passing through the pylorus into the stomach.

The anchor position is preferably selected to avoid obstruction of the bile-releasing function of the ampulla of vader, although the construction of the anchor might be such as to allow its placement over the ampulla without interference with the ampulla's function. In preferred methods, the deployment system is introduced into the body via the oral cavity, passed through the esophagus and into the stomach, and then moved through the pyloric sphincter into the small intestine. In alternative methods, the deployment system may be advanced into the stomach using a small perforation through the abdominal wall and into the stomach, and then passed into the small intestine from the stomach.

Figure 2A:
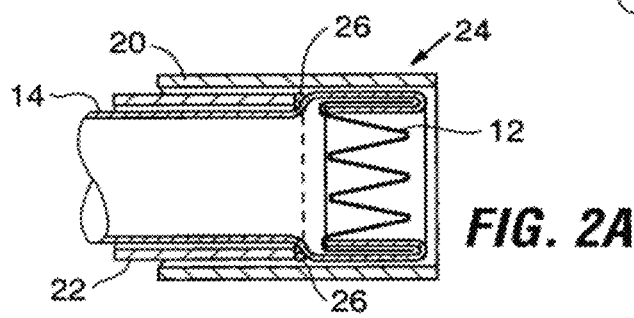
FIGS. 2A-2C are cross-sectional side views illustrating one embodiment of a method for deploying an inverted post-pyloric sleeve in the small intestine of a patient.
Figure 2B:
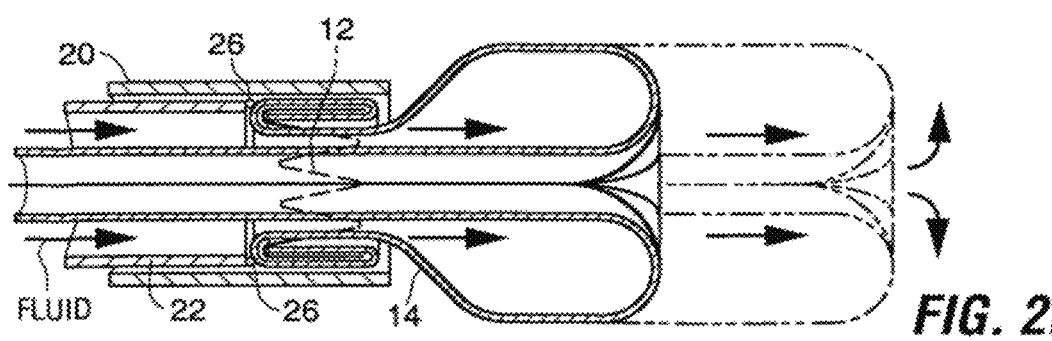
Figure 2C:
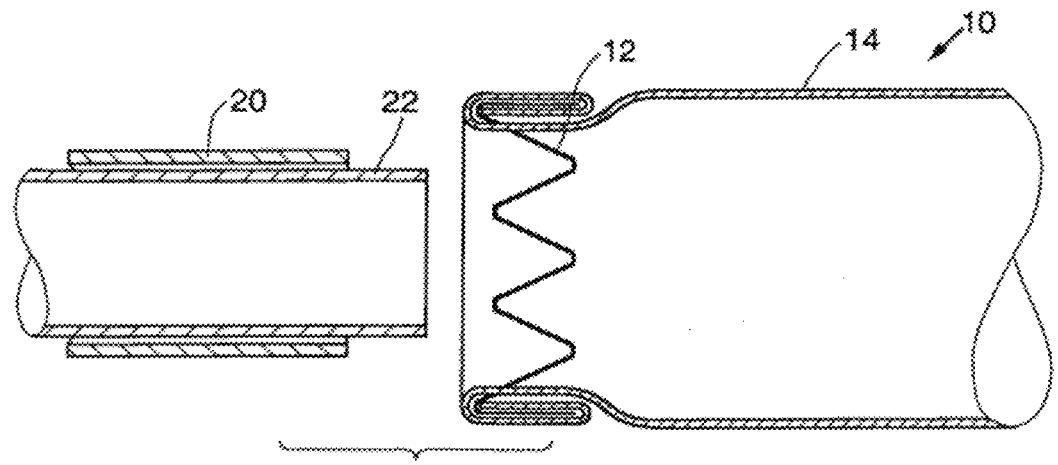

One example of a deployment method, shown in FIGS. 2A-2C, uses an outer sheath 20 axially positioned over an inner sheath 22. The outer sheath 20 extends distally from the inner sheath 22, leaving room for the anchor 12 of the post-pyloric sleeve 10 to be contained in a collapsed position within the distal end 24 of the outer sheath 20. The sleeve 14 is positioned within the inner sheath 22, extending in a proximal direction as shown, and is inverted such that its inner surface faces outwardly. Sleeve 14 may be singly inverted, such that its distal end (meaning the end that is positioned furthest along the intestine from the stomach once the sleeve is fully deployed) is in the most proximal position for deployment, or it may be inverted multiple times within its lumen. An optional seal 26 on the inner sheath 22 is in sealing contact with the sleeve 14.

With the distal end of the outer sheath 20 positioned in the small intestine, fluid such as water or gas is directed through the inner sheath 22 as shown in FIG. 2B. The fluid exerts pressure against the inverted sleeve 14, causing the sleeve to evert through the anchor 12 until the full length of the tube has deployed. As the sleeve is deployed, the inner and outer sheaths 20, 22 preferably remain in a fixed position, allowing the sleeve to roll out of the inner sheath into the intestinal lumen without sliding relative to the surface of the intestinal wall. Once the sleeve is deployed, the outer sheath 20 is withdrawn, causing the anchor 12 to pass out of the sheath 20 and to self-expand into engagement with the intestinal wall. If preferred, the anchor 12 may alternatively be deployed before the sleeve is everted.

Figure 2D:
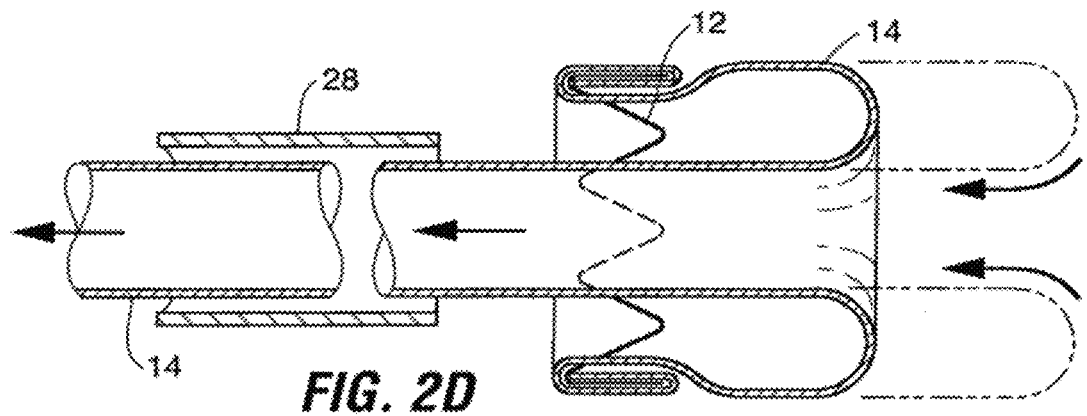
FIGS. 2D and 2E illustrate a method for retrieving the sleeve deployed in FIGS. 2A-2C.

Removal of the implant 10 from the intestine is achieved by engaging a portion (e.g. the distal end, or a more proximal or intermediate portion) of the sleeve 14 such as by advancing a grasping instrument through the sleeve 14 and engaging the sleeve with the grasping instrument. The engaged portion of the sleeve is pulled through the sleeve's inner lumen as shown in FIG. 2D causing the sleeve 14 to invert and to pass into a capture tube 28.

Figure 2E:
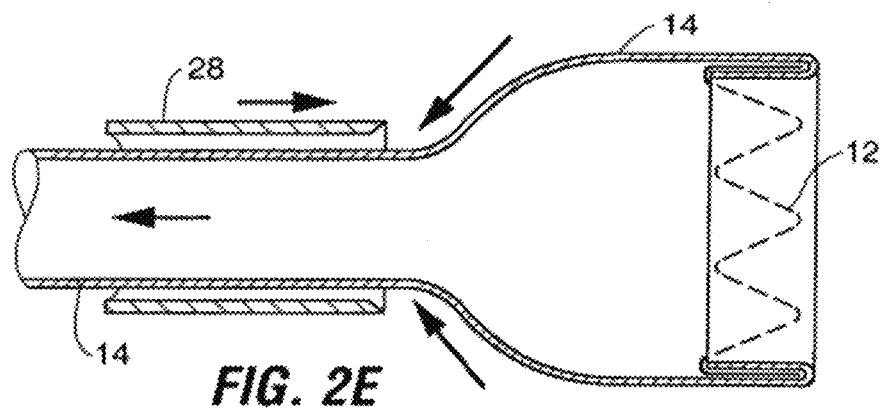

The capture tube 28 is advanced over the grasping instrument to a position near the anchor 12, and traction is applied to the sleeve 14 as shown in FIG. 2E to draw the anchor 12 into a collapsed position within the capture tube.

Figure 3A:
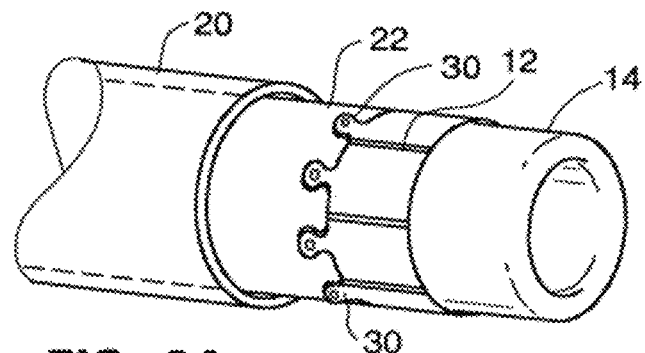
FIG. 3A is a perspective view of an inverted post-pyloric sleeve, illustrating features for retaining the sleeve on a deployment tube. The outer sleeve is shown cut away to allow the inner sleeve, anchor, and tabs to be viewed.
Figure 3B:
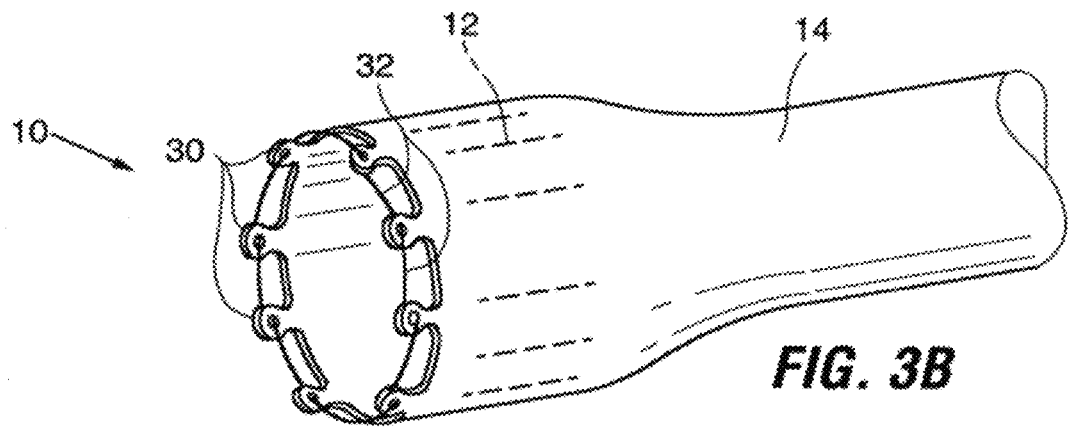
FIG. 3B is a perspective view of the sleeve of FIG. 3A deployed and separated from the deployment tube.
Figure 3C:
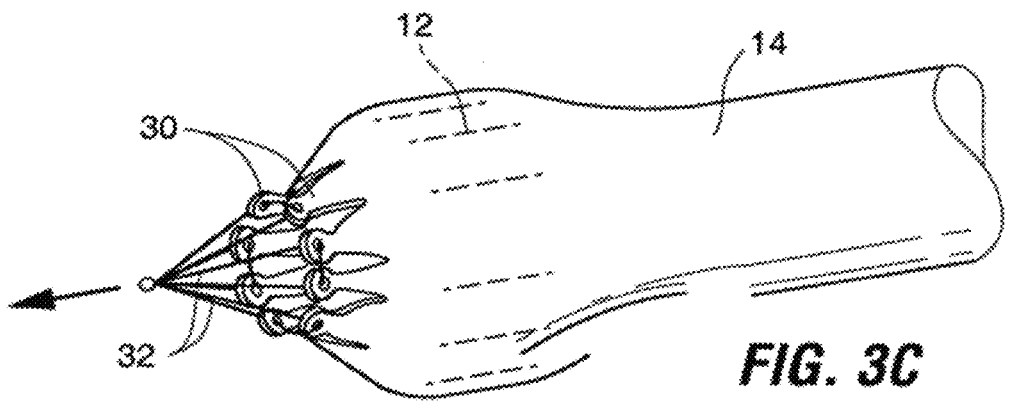
FIG. 3C is a perspective view illustrating a method of collapsing the sleeve of FIG. 3A for withdrawal from the intestine.

As illustrated in FIGS. 3A and 3B, the implant may include a plurality of tabs 30 (on the sleeve 14 or the anchor 12) that engage with the inner sheath 22, preferably forming a seal. Once the implant 10 is deployed as shown in FIG. 3B, the tabs 30 may remain on the implant, or they may bioerode or be removed in another way. If the tabs 30 remain in place, they might later be cinched together using a strand of suture 32 as in FIG. 3C and used to withdraw the implant 10 into a capture tube (not shown).

Figure 4:
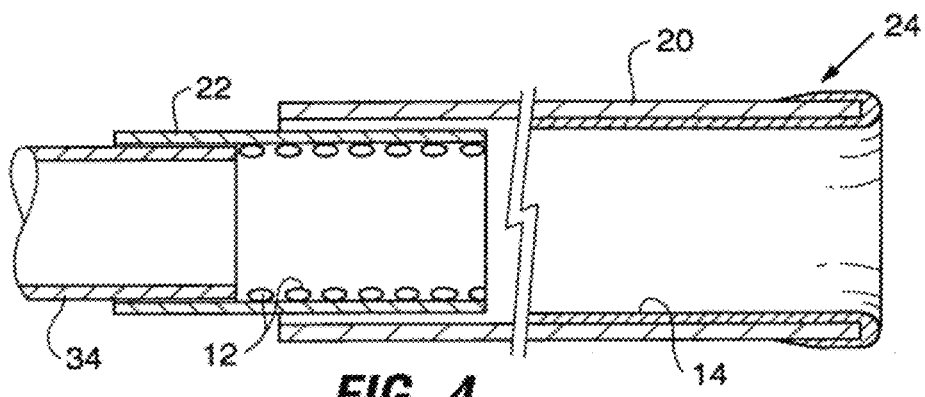
FIG. 4 illustrates an alternative method for deploying an inverted sleeve using an independent anchor.
Figure 5:
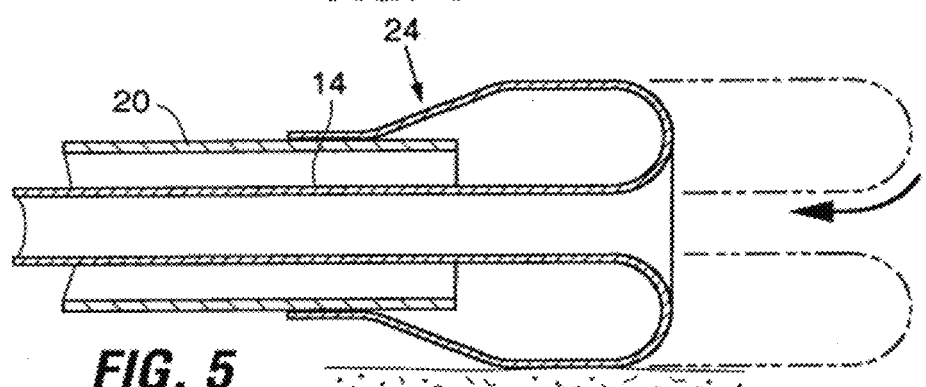
FIG. 5 is a cross-sectional side view illustrating deployment of the sleeve of FIG. 4.

In alternate implant designs, the sleeve 14 and anchor may be separate components as shown in FIG. 4. A system for deploying this modified implant includes an outer sheath 20 having the proximal end of the sleeve 14 mounted to its distal end 24 and inverted to extend through the lumen of the sheath 20. As shown in FIG. 5, fluid is used to evert the sleeve 14 in a manner similar to that described above. Referring again to FIG. 4, once the sleeve 14 has been positioned in the intestine, an inner sheath 22 having anchor 12 collapsed within it is advanced to the proximal end of the sleeve 14. An anchor pusher 34 is used to push the anchor from the inner sheath 22, causing the anchor to expand and to trap the proximal end of the sleeve between the anchor and the intestinal wall.

Figure 6A:
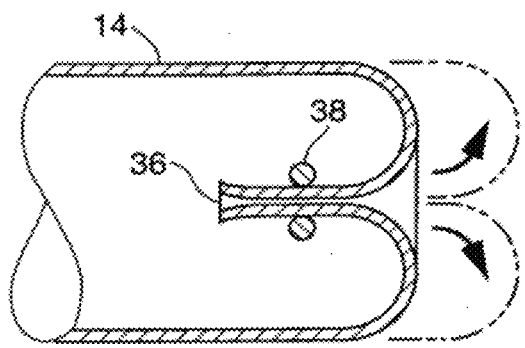
FIGS. 6A and 6B illustrate deployment of the distal end of a sleeve and release of the sealing ring.
Figure 6B:
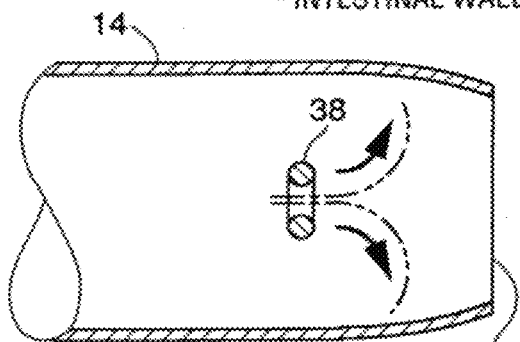

FIG. 6A illustrates an implant 10 in the inverted position in the process of being deployed. As shown, sealing the distal end 36 of the sleeve 14 can facilitate deployment as fluid pressure everts the sleeve. The distal end of the sleeve may be bunched, folded, twisted, rolled or simply compressed, and its position retained by an optional clamping device 38 such as an o-ring, staple, clip, suture etc. which will release from the sleeve upon full deployment as shown in FIG. 6B. The clamping device 38 may be bioerodable or constructed to be small enough to pass through the intestinal tract. Dissolvable or temporary adhesives or other agents may be used with, or as an alternative to, the clamping device 38.

Figure 7A:
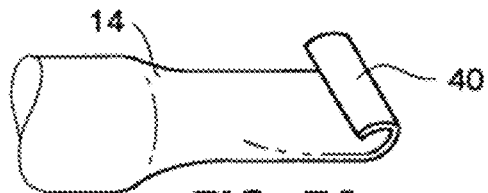
FIGS. 7 A and 7B illustrate steps for folding a distal end of a sleeve to create a seal.
Figure 7B:
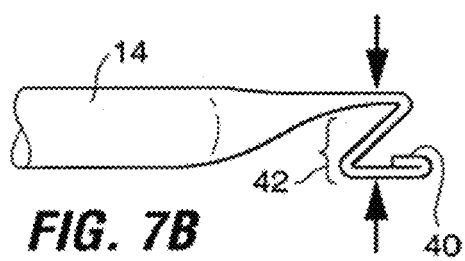

As yet another alternative shown in FIGS. 7A and 7B, a fold 40 can be placed in the distal end 36 of the sleeve, and then a Z-fold 42 formed to seal the distal end 36.

Figure 6C:
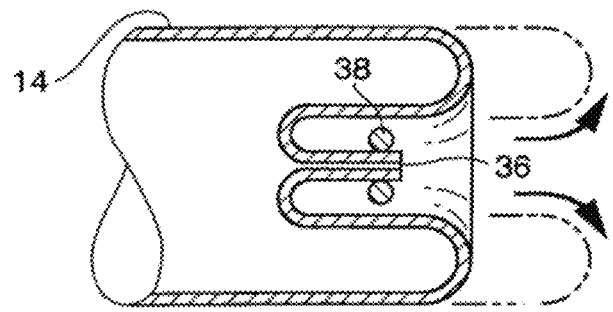
FIG. 6C is similar to FIG. 6A but shows a different arrangement for the distal end of the sleeve.

In a preferred arrangement, the clamping device is an o-ring anchored to the sleeve 14 by friction caused by an interference or compression fit. The everting pressure acts upon the interface after the sleeve has fully everted (FIG. 6B), preventing an unintended pressure loss or failure to deploy. The o-ring is proportioned to readily pass through the digestive system after it detaches from the sleeve. FIG. 6C is similar to FIG. 6A but shows a different arrangement for the distal end of the sleeve prior to release of the o-ring 38.

Figure 8:
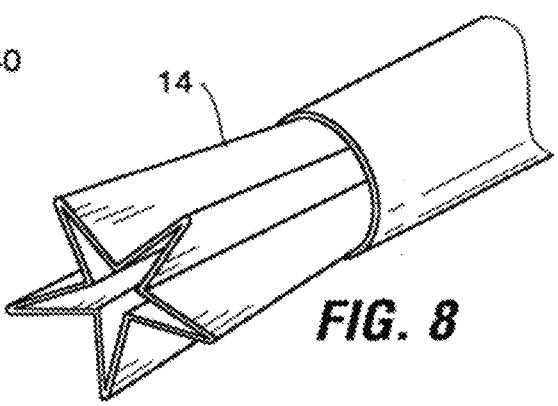
FIG. 8 illustrates a sleeve folded in a star pattern.

In some embodiments, it may be useful to pleat the sleeve 14 with controlled, longitudinal folds, such as those forming a star-shaped or other symmetrical cross-section as shown in FIG. 8 so as to minimize binding of the sleeve 14 as it everts during deployment.

Figure 9A:
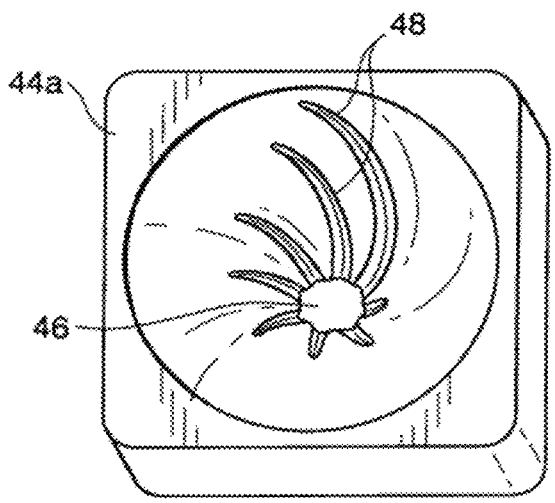
FIGS. 9A and 9B are examples of folding jigs that may be used to create a star pattern similar to that shown in FIG. 8.
Figure 9B:
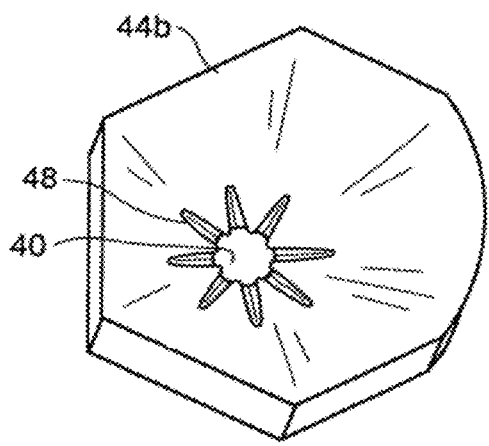
Figure 9C:
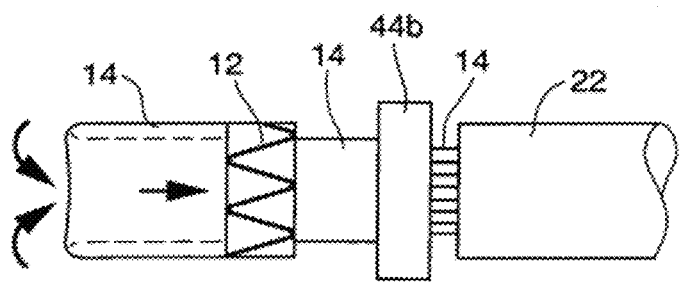
FIG. 9C is a side elevation view showing a sleeve being inverted, passed into the jib of FIG. 9B for folding, and being drawn in its folded state into a deployment sleeve.

This type of folding pattern can be facilitated by threading the sleeve through a jig 44a, 44b of the type shown in FIGS. 9A and 9B. The jig 44a, 44b includes an opening 46 and slits 48 radiating from the opening 46. Threading the sleeve through one of the jigs causes the sleeve to fold into a star-shaped pattern. Preferably, the sleeve is fed directly from the jig into a retention sheath to retain the folded pattern. For example, as shown in FIG. 9C, as the sleeve 14 is being inverted and loaded into sheath 22, its distal end is drawn into its own interior lumen, pulled through the lumen of the anchor 12, into the jig 44b to place the folds/pleats in the sleeve 14, and pulled further (now folded/pleated) into the sheath 22.

The next sequence of embodiments make use of the natural peristaltic movement of the intestine to carry the distal end of the sleeve 14 into its deployed position within the intestine. As with the previously described embodiments, use of these methods typically involves advancing the deployment system containing the implant through the pylorus and then deploying the sleeve and anchor using the deployment system. With each of these embodiments, the anchor may be engaged with the intestinal wall either prior to or after deployment of the sleeve.

A peristaltically deployed implant may be similar to the implant 10 of FIG. 1A, but it preferably includes a weighted element capable of being engaged by the peristaltic action of the intestine such that it will be carried by peristalsis through the intestine. The element is selected to be one having a mass or size that allows it to be better engaged by peristaltic activity than the sleeve material itself.

Figure 10A:
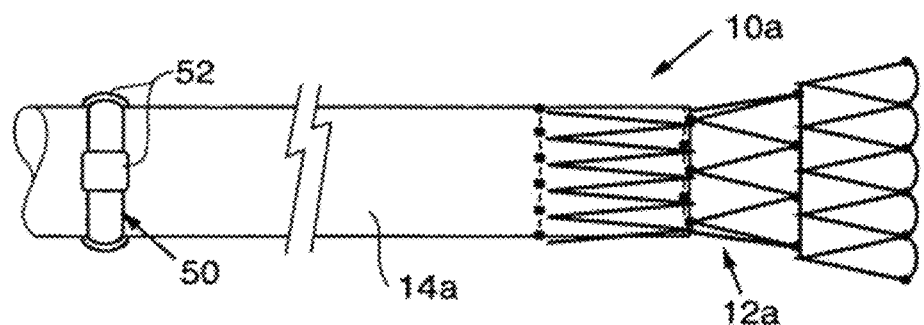
FIG. 10A is an example of a post-pyloric sleeve configured for peristaltic deployment.

Referring to FIG. 10A, implant 10a may be modified to include an o-ring 50 on its distal end. O-ring 50 may be formed of any suitable material. In one embodiment, it may be thick silicone rubber or another non-degradable material, or it may be a material that bioerodes or dissolves over time. The o-ring might be anchored to the sleeve 14a such that it will remain in place until the sleeve is removed from the body, or it can be temporarily attached to the sleeve (e.g. using dissolvable adhesives or sutures) so that it will detach from the sleeve following deployment and pass through the digestive system. The o-ring 50 can include radiopaque markers 52 such as platinum tubes crimped onto the o-ring.

Figure 16:
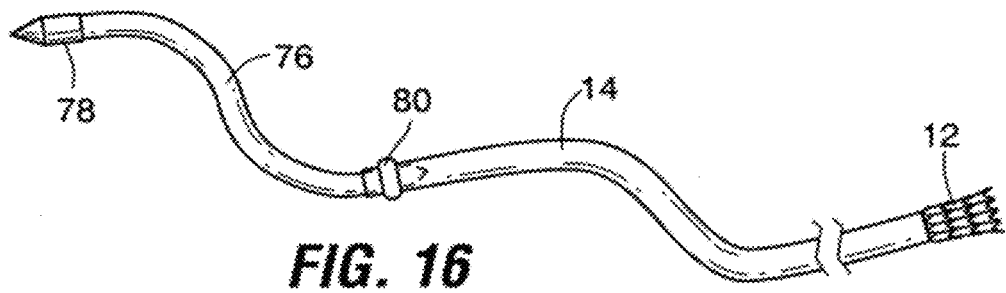
FIG. 16 illustrates a post-pyloric sheath in a compressed position and carried by a deployment catheter.

Other embodiments for deploying the sleeve using peristalsis may include packaging the implant in a tear-away sheath, advancing the packaged sheath beyond the pylorus, and removing the sheath (e.g. using a pullwire). Another embodiment shown in FIG. 16 employs a lead tube 76 having an atraumatic tip 78 of sufficient size and mass to be carried through the intestine by peristalsis. Lead tube 76 is coupled to the distal end of the sleeve 14 by an o-ring 80 or other temporary means. Both the lead tube 76 and the o-ring 78 may be bioerodible or passable from the system. As with the other disclosed embodiments, this system can be used to move the sleeve through the intestine either before or after the anchor 12 is engaged with the intestinal wall.

Figure 10B:
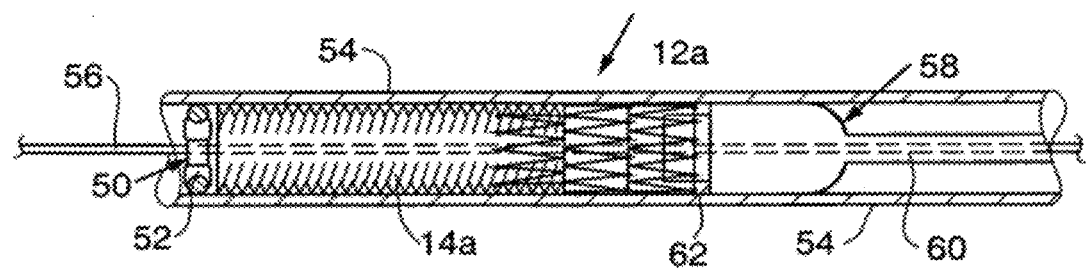
FIG. 10B illustrates the sleeve of FIG. 10A in a deployment sheath together with a pusher rod.
Figure 10C:
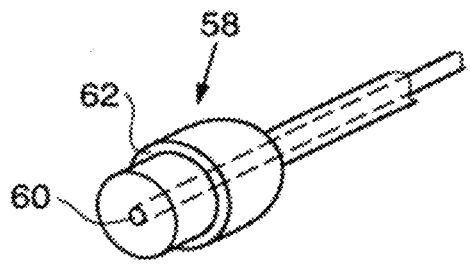
FIG. 10C is a perspective view showing the pusher rod of FIG. 10B.

Referring to FIG. 10B, a deployment system for the implant 10a of FIG. 10A may include a sheath 54 having the implant 10a within it. The sleeve 14a of the implant 10a may be accordion pleated within the sheath 54 as shown, or it may be simply crumpled into the sheath, or folded in some other way. Pleating may be in a uniform pattern, or different parts of the sleeve may be more tightly or loosely pleated to encourage deployment. During use, the sheath 54 as assembled in FIG. 10B is preferably passed over a guidewire 56 that has been guided through the pyloric sphincter. The sheath 54 is positioned with its distal end positioned past the pyloric sphincter, and a push rod 58 is used to push the implant 10a such that at least part of the sleeve 14a exits the sheath 54. During this step of deployment, the push-rod may be used to cause only the distal end of the sleeve 14a to exit the sheath 54, or to cause the entire sleeve 14a but not the anchor 12a to exit the sheath 54, or to fully expel the implant 10a (including the anchor) from the sheath 54. Details of an exemplary push rod 58, which may include a lumen 60 for accommodating the guidewire and a shoulder 62 for engaging the anchor 12a, are shown in FIG. 10C.

Figure 10D:
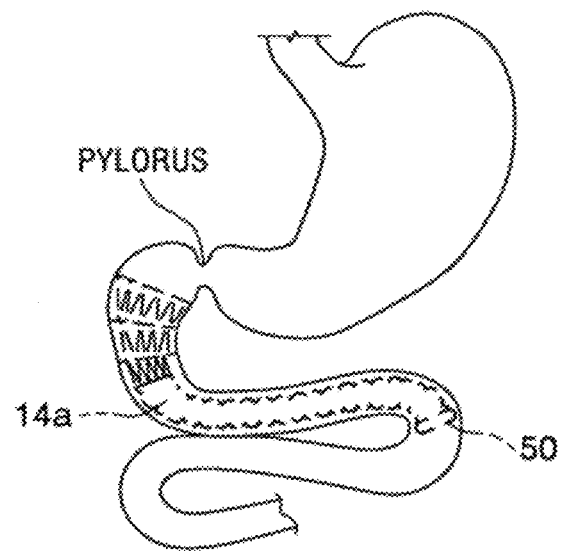
FIG. 10D illustrates the sleeve of FIG. 10A with the anchor deployed and the sleeve in the process of deploying via peristalsis.

When the o-ring 50 passes into the intestine, it is carried through the intestine by peristalsis, gradually expanding the sleeve 14a as shown in FIG. 10D. If the anchor 12a was not previously deployed, the push rod 58 may be subsequently used to release the anchor during or after full deployment of the sleeve 14a.

With respect to embodiments whose deployment is achieved using peristalsis, airds may be employed to enhance or increase natural peristalsis to facilitate deployment. For example, in the system shown in FIG. 10B, guidewire 56 may function as a stimulating lead having an electrode that may be energized when placed into contact with tissue at selected regions of the intestine or stomach so as to regulate peristaltic contractions. Alternatively, guidewire 56 may include a delivery lumen for delivering agents suitable for enhancing peristalsis. In either case, a separate electrode lead or fluid delivery lumen, rather than the guidewire, may be used to regulate peristalsis.

Figure 11A:
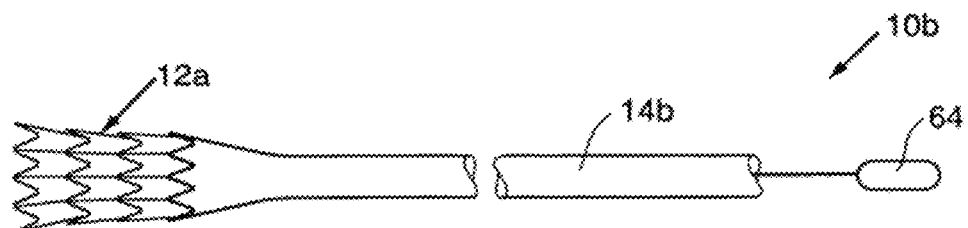
FIG. 11A is a plan view of an alternative sleeve having features for peristaltic deployment.
Figure 11B:
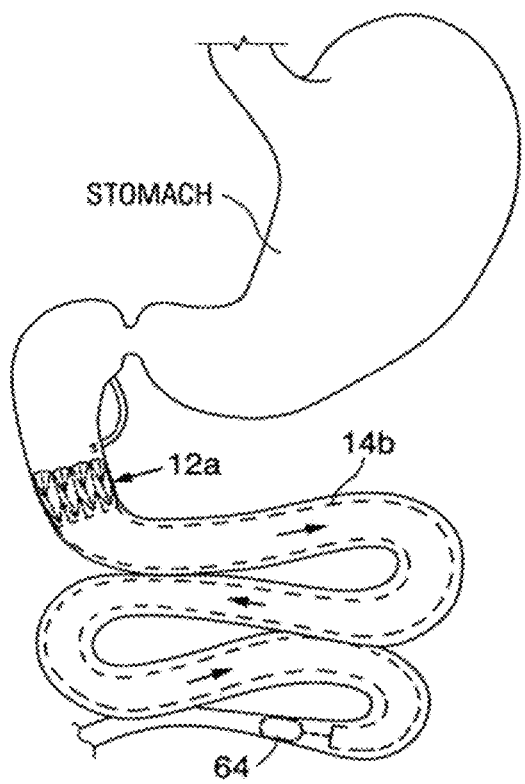
FIG. 11B illustrates the sleeve of FIG. 11A deployed in the small intestine.

FIGS. 11A and 11B illustrate an alternative implant 10b in which the o-ring of FIG. 10A is replaced with a dissolvable member 64 such as a dissolvable/erodible gelatin capsule tethered to the distal end 36 of the sleeve 14b. Deployment of the FIG. 11A may proceed as described in connection with the FIG. 10A embodiment.

Figure 12:
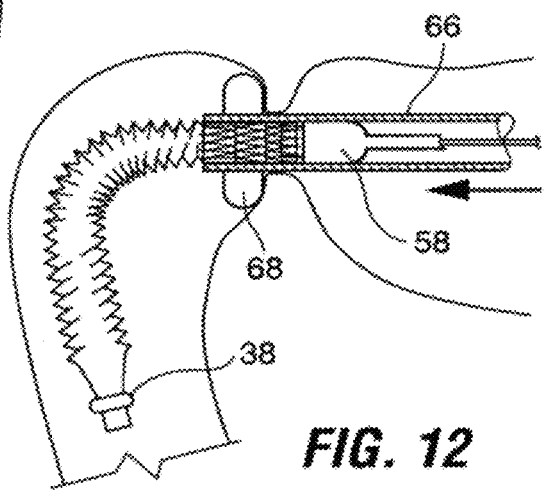
FIG. 12 illustrates deployment of a post-pyloric sleeve using fluid pressure.
Figure 13:
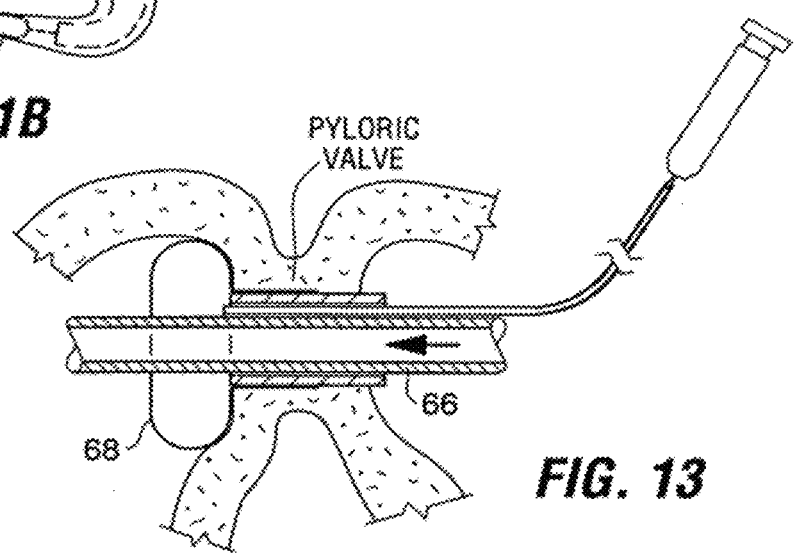
FIG. 13 schematically illustrates sealing of the pyloric sphincter using the pyloric seal of FIG. 12.

In an alternative deployment method shown in FIG. 12, a deployment sheath 66 containing the implant 10 is passed through the pylorus. The sleeve 14 of the implant is accordion folded within the sheath 66, and the implant is sealed using an o-ring or other seal 38 (see those described in connection with FIGS. 6A-7B) at the distal end of the sleeve 14. Water or other suitable fluid is directed into the sheath 66 and through the implant 10. The fluid pressure within the sealed sleeve 14 causes the sleeve to unfold within the intestine. Once the sleeve is fully deployed, the seal 38 is released. As best illustrated in FIG. 13, the sheath 66 may include an annular balloon 68 expandable beyond the pylorus to seal the pylorus against backflow of water. A push rod 58 may be used to expel the anchor 12 from the sheath 66 either before or after the sleeve is deployed.

Figure 14A:
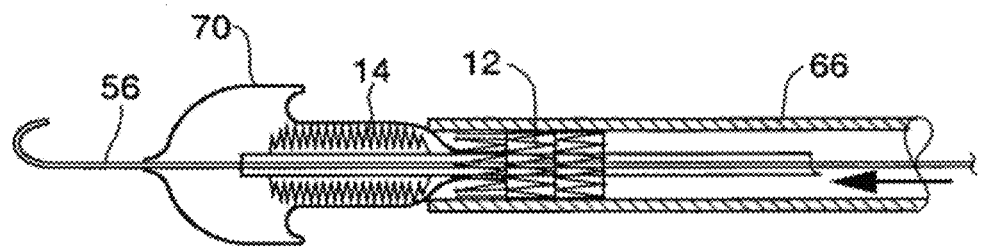
FIG. 14A illustrates a post-pyloric sleeve carried by an alternative deployment system utilizing a capsule or cassette for containing the sleeve.
Figure 14B:
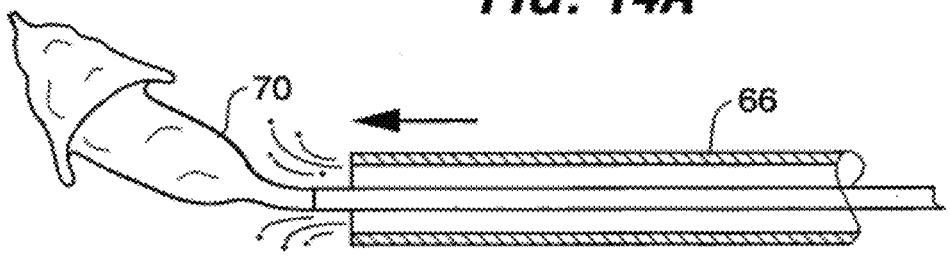
FIG. 14B shows an alternative to the cassette of FIG. 14A shaped to facilitate fluid propulsion of the cassette within the intestine.
Figure 15A:
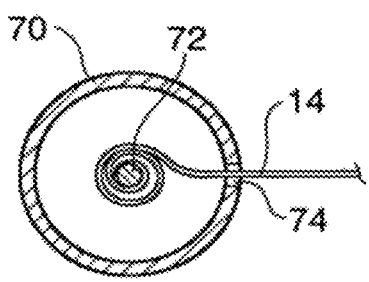
FIG. 15A illustrates rolling of a post-pyloric sleeve into a cassette for deployment.

In a variation of the FIG. 12 embodiment shown in FIG. 14A, the sleeve 14 may be folded, compressed or rolled to fit into a capsule or cassette 70 positioned distally of a sheath 66 housing the compressed the anchor 12. The capsule 70 is advanced by peristalsis or by fluid pressure (FIG. 14B), allowing the sleeve to pay out from the capsule as it advances within the intestine. Once the sleeve is deployed, the capsule detaches from the sleeve and passes from the body. FIG. 15A illustrates that the sleeve can be rolled into the capsule by engaging the sleeve with a mandrel 72 and rotating the mandrel about its longitudinal axis.

Figure 15B:
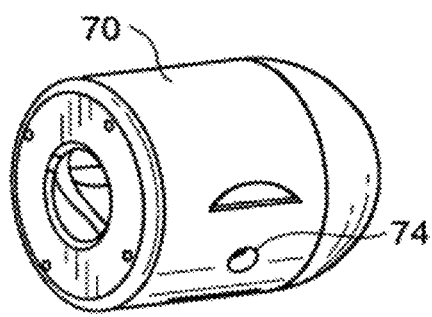
FIGS. 15B and 15C are a perspective view and a cross-sectional side view of the cassette of FIG. 15A.
Figure 15C:
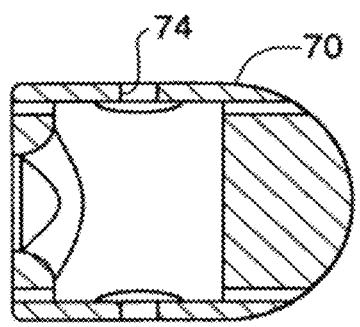

As more easily seen in FIGS. 15B and 15C, capsule 70 includes holes 74 for receiving the mandrel.

Figure 17:
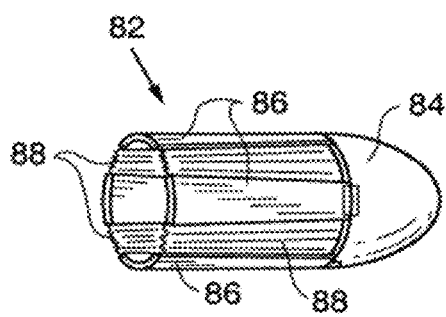
FIGS. 17 and 18 illustrate a fluid-advanceable device for carrying a post-pyloric sleeve through the small intestine.
Figure 18:
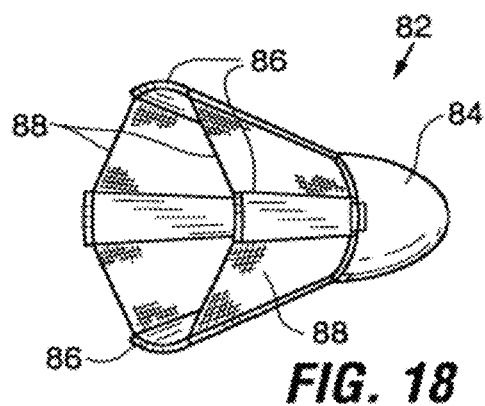
Figure 19:
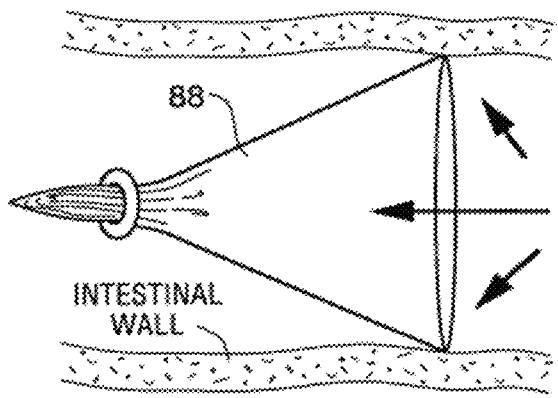
FIG. 19 illustrates an alternative fluid-advanceable device passing through an intestinal lumen.
Figure 20:
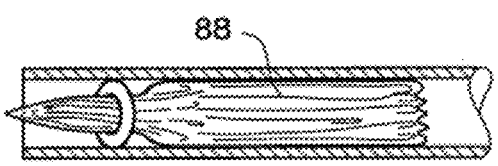
Figure 21:
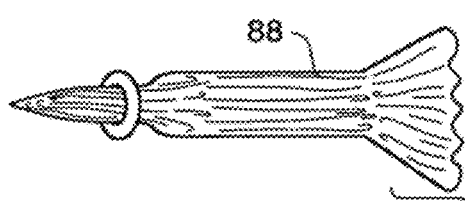
Figure 22A:
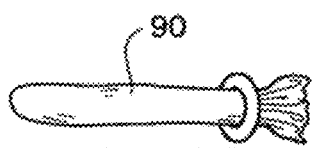
Figure 22B:
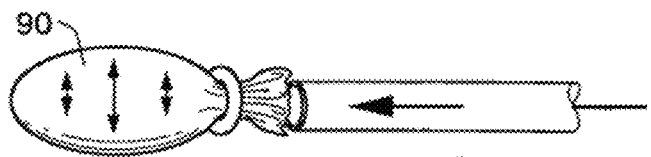

FIGS. 17 through 23B illustrate the use of fluid to propel an expandable component through the intestine. In these embodiments, a guidewire, shown in FIG. 22D, may be tethered to the expandable component so that the sleeve 14 may later be passed over the guidewire, or the sleeve itself may be tethered to the expandable component. As shown in FIGS. 17 and 18, the expandable component may take the form of a shuttlecock 82 having an atraumatic tip 84. A plurality of struts 86 are hinged to the tip 84, and webbing extends between the struts. When released from the constrained position shown in FIG. 17, the struts 86 spring to the expanded position shown in FIG. 18, expanding the webbing 88 into a conical shape. Fluid directed as shown in FIG. 18 will impart pressure against the interior of the expanded cone, causing the expandable component 82 to advance through the intestine. In alternative configurations, the expandable component may have a parachute type configuration 88 that is expandable as a result of fluid pressure as shown in FIGS. 19-21. In another embodiment, the expandable component may be an inflatable balloon 90 that is expanded within the intestinal lumen and then propelled within the intestine by fluid pressure as shown in FIG. 22C. This design may be modified to include a flap valve 92 as shown in FIGS. 23A and 23B. As water is pulsed towards the balloon 90 to advance it within the intestine, the water contacts the flap valve 92 to propel the balloon. In between pressure pulses of the fluid system, the flap 92 will open as in FIG. 23B if necessary to relieve backpressure within the intestine.

As discussed in connection with FIG. 10B, some implantation methods may be performed by tracking the sleeve over a guidewire alone or in combination with other deployment methods. FIGS. 24A-26 illustrate and describe methods that may be used to manipulate a guidewire through the intestines.

Figure 24B:
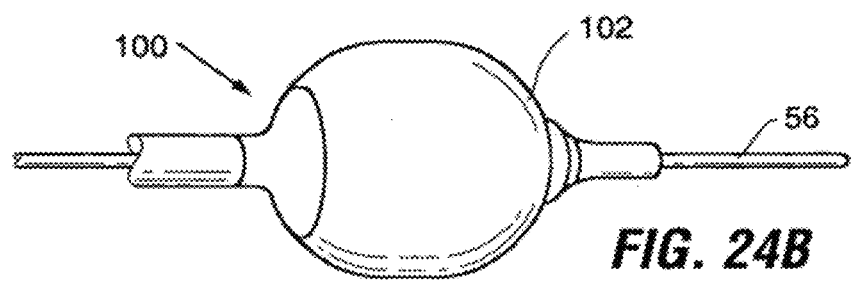
Figure 24C:
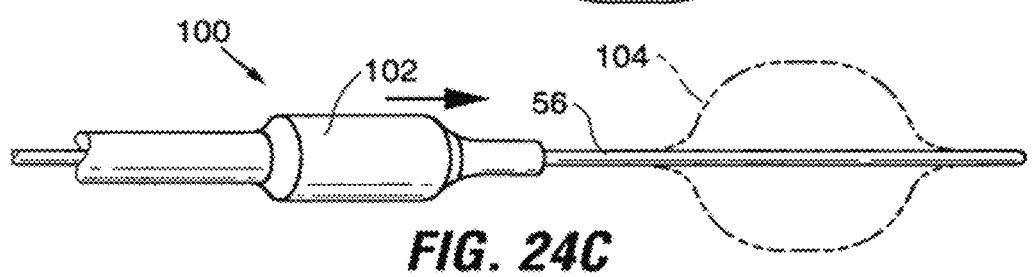

Referring to FIG. 24, guidewire 56 extends through a catheter 100 having an inflatable balloon 102 at the distal end. To deploy the guidewire, the catheter 100 is moved into the intestine and the balloon 102 is inflated into contact with the surrounding intestinal walls.

The guidewire is passed though the catheter until it extends from the distal end of the catheter 100. The balloon is next deflated, the catheter advanced further within the intestine, the guidewire advanced, etc. until the guidewire reaches the desired location in the intestine (e.g. beyond the pylorus). The catheter may include an optional anchoring balloon 104 (shown in dashed lines in FIG. 24C) that is inflatable to anchor the wire in place within the intestine as the catheter is advanced over the wire. In alternative guidewire placement methods, a balloon of this type may be used to carry the guidewire through the intestine using peristalisis or fluid pressure as disclosed above in connection with sleeve deployment.

Once the guidewire is in position, an intestinal sleeve 14 and anchor 12 (preferably packaged within a sheath as described) are tracked along the guidewire to the desired location in the body, at which time they may be released from the sheath and anchored within the intestine.

Figure 25A:
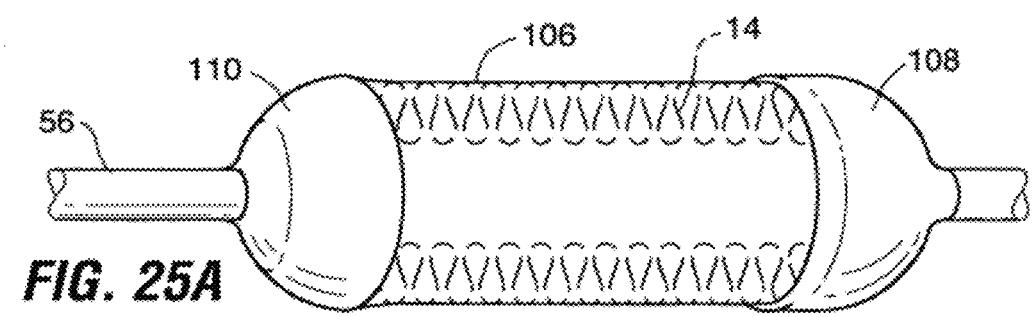
FIGS. 25A-25C illustrate a modification to the system of FIG. 24A-C for use in deploying an intestinal sleeve.
Figure 25B:
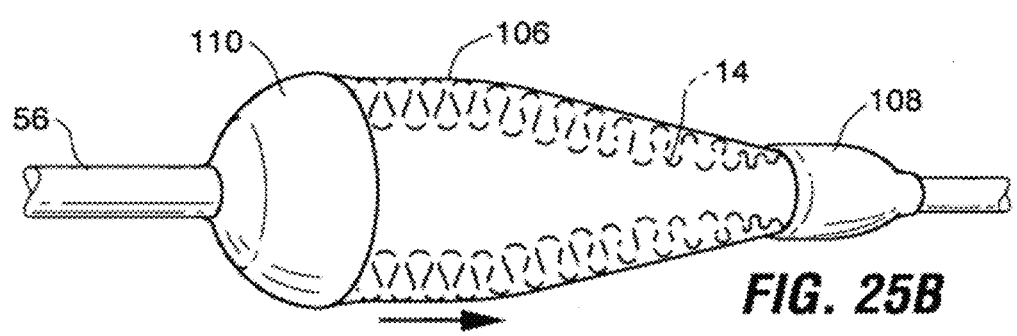
Figure 25C:
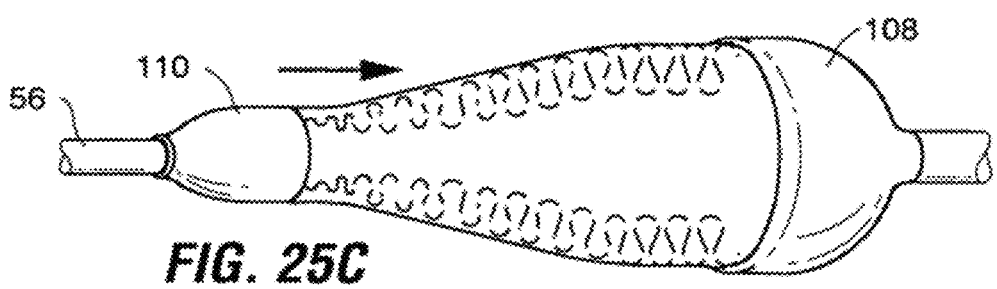

FIGS. 25A-25C illustrate that sequential inflation, advancement and deflation of balloons may be used to deploy the sleeve 14 itself. For example, as shown sleeve 14 may be positioned within a sheath 106 having distal and proximal balloons 108, 110. Proximal balloons 110 is inflated into contact with the surrounding intestinal walls to prevent rearward movement of the sheath 106 while the distal section of the sheath (including deflated distal balloon 108) is advanced over the guidewire 56. Next, distal balloon 108 is inflated into contact with the surrounding walls, and proximal balloon 110 is deflated and advanced, causing the sheath 106 to inch-worm along the guidewire 56. Once in the proper position, the sheath 106 is removed from the sleeve 14 (e.g. by using a pusher to push the sleeve from the sheath as discussed above, or by perforating the sheath, etc.), causing the anchor to expand and engage the surrounding intestinal walls.

Figure 26A:
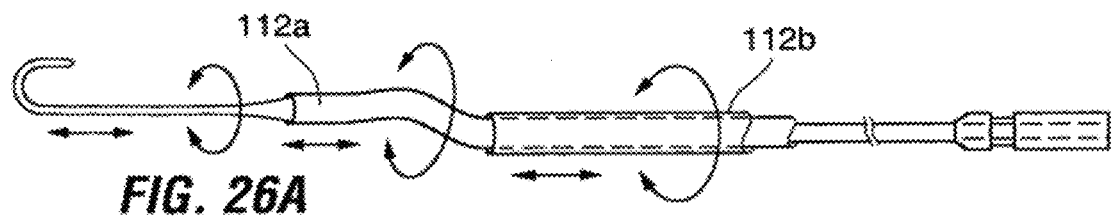
FIG. 26A illustrates a torquable catheter system for use in moving a guidewire through an intestinal tract.
Figure 26B:
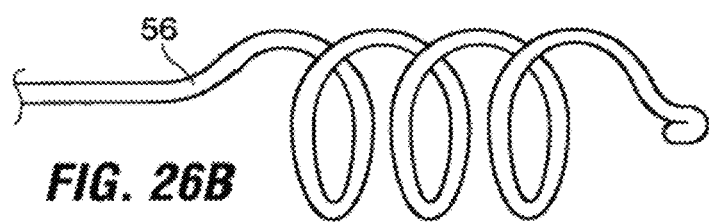
FIG. 26B is a side elevation view of a distal end of a guidewire.
Figure 27:
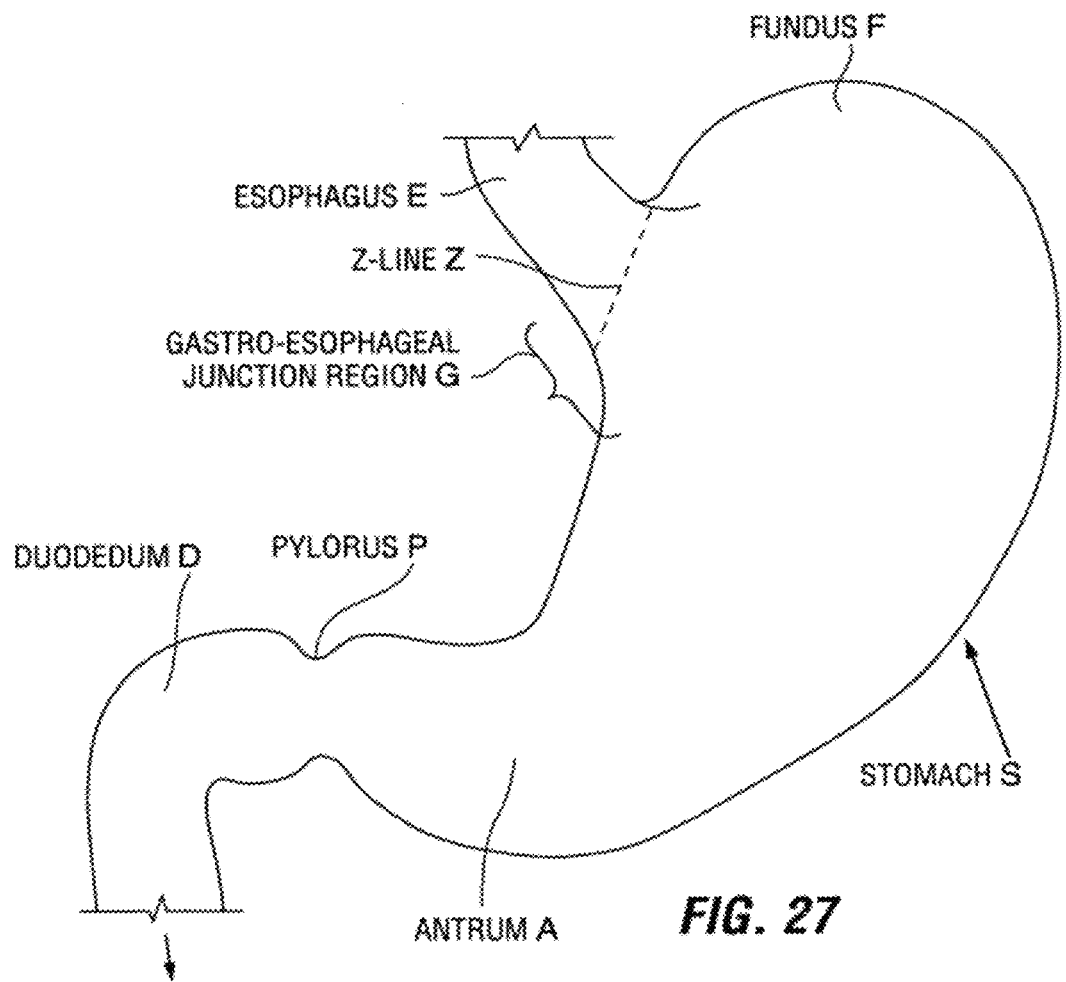
FIG. 27 is a schematic illustration of a human stomach and a portion of the small intestine.

Any of the disclosed embodiments may employ an endoscope to allow visualization of the implantation procedure. The guidewire or associated instruments or implants may be passed through the working channel of a flexible endoscope, or through other access tubes passed through the mouth and esophagus. Manipulation and steering of a guidewire 56 through the tortuous intestinal system may be accomplished by passing the guidewire through one or more telescoping catheters 112a, 112b (FIG. 26A) that function to change the orientation of the catheter as it is advanced. For example, inner catheter 112a may have a pre-shaped distal end as shown that may be used to steer the guidewire, and outer catheter 112b may be a straight catheter that will retain catheter 112a in a straight orientation when the inner catheter 112a is drawn inside it. The distal end of the guidewire 56 may include a supple distal tip as shown in FIG. 26B to minimize trauma to surrounding tissue.

Any of the above implants and systems may be packaged with instructions for use setting forth methods for implanting the implants in accordance with methods of the type disclosed herein, for the purpose of inducing weight loss and/or treating diabetes by causing the implant to restrict absorption of ingested material such as carbohydrates, nutrients, etc.

It should be recognized that a number of variations of the above-identified embodiments will be obvious to one of ordinary skill in the art in view of the foregoing description. Moreover, the various features of the embodiments that have been described may be combined in various ways to produce numerous additional embodiments.

Accordingly, the invention is not to be limited by those specific embodiments and methods of the present invention shown and described herein. Rather, the scope of the invention is to be defined by the following claims and their equivalents.

Any and all patents, patent applications and printed publications referred to above are incorporated by reference.

We claim:

1. A method for deploying an intestinal sleeve in a patient, comprising:
   expanding a device from a first position to an expanded position in an intestine of the patient, wherein the device includes a plurality of struts with material between adjacent struts;
   causing fluid to flow in a proximal-to-distal direction towards the device to contact the device and to move the device distally within the intestine; and
   positioning an intestinal sleeve in the intestine proximal to the device.

2. The method of claim 1, further comprising coupling the intestinal sleeve to the device prior to causing fluid to flow to move the device distally.

3. The method of claim 2, wherein the sleeve is coupled to the device by a tether.

4. The method of claim 1, further comprising coupling a guidewire to the device prior to causing fluid to flow to move the device distally, wherein positioning the intestinal sleeve in the intestine includes passing the sleeve over the guidewire.

5. The method of claim 1, wherein the plurality of struts are configured to expand the device from the first position to the expanded position.

6. The method of claim 1, wherein the device forms a conical shape in the expanded position.

7. A method for deploying an intestinal sleeve in a patient, comprising:
   inserting a device and a sleeve into an intestine of the patient, wherein the sleeve is coupled to the device and extends in a proximal direction from the device;
   expanding the device from a first position to an expanded position; and
   causing fluid to flow in a proximal-to-distal direction towards the device to contact the device and to move the device distally in the intestine.

8. The method of claim 7, wherein the sleeve is coupled to the device by a tether.

9. The method of claim 7, wherein the device includes a plurality of struts with material between adjacent struts.

10. The method of claim 9, wherein the plurality of struts are configured to expand the device from the first position to the expanded position.

11. The method of claim 7, wherein the device forms a conical shape in the expanded position.

12. The method of claim 7, further comprising using fluid to expand the device from the first position to the expanded position.

13. The method of claim 7, wherein the device includes a balloon.

14. The method of claim 7, wherein the device includes a valve.

15. The method of claim 7, wherein causing fluid to flow to move the device includes using pulses of fluid pressure.

* * * * *